(12) United States Patent
Chen et al.

(10) Patent No.: US 6,723,285 B2
(45) Date of Patent: Apr. 20, 2004

(54) FOOD FRESHNESS INDICATOR

(76) Inventors: Natali Chen, P.O. Box 1317, Bat-Hefer (IL); Nadav Chen, P.O. Box 1317, Bat-Hefer (IL); Naaman Chen, P.O. Box. 1317, Bat-Hefer (IL)

( * ) Notice: Subject to any disclaimer, the term of this patent is extended or adjusted under 35 U.S.C. 154(b) by 99 days.

(21) Appl. No.: 09/829,962

(22) Filed: Apr. 11, 2001

(65) Prior Publication Data

US 2002/0151075 A1 Oct. 17, 2002

(51) Int. Cl.[7] .................. G01N 21/00; G01N 33/02
(52) U.S. Cl. .................. 422/58; 436/21; 436/22; 436/23; 436/24; 422/55; 422/50; 422/61
(58) Field of Search .................. 422/50, 55, 74; 436/20–24

(56) References Cited

U.S. PATENT DOCUMENTS

| | | | |
|---|---|---|---|
| 3,999,946 A | | 12/1976 | Patel et al. .................. 422/56 |
| 4,003,709 A | * | 1/1977 | Eaton et al. .................. 422/86 |
| 4,212,153 A | | 7/1980 | Kydonieus et al. .......... 368/62 |
| 4,292,916 A | | 10/1981 | Bradley et al. ............. 116/205 |
| 4,382,700 A | | 5/1983 | Youngren .................... 374/102 |
| 4,859,360 A | | 8/1989 | Suzuki et al. ............ 252/299.7 |
| 5,460,117 A | | 10/1995 | Loustaunau ................. 116/218 |
| 5,976,827 A | * | 11/1999 | Jeffrey et al. .................. 435/34 |
| 5,997,927 A | | 12/1999 | Gics ........................... 426/383 |
| 6,372,182 B1 | * | 4/2002 | Mauro et al. .................. 422/56 |
| 6,373,786 B1 | * | 4/2002 | Kagan et al. .................. 368/10 |
| 6,495,368 B1 | * | 12/2002 | Wallach ....................... 436/20 |
| 2002/0034475 A1 | * | 3/2002 | Ribi ........................... 424/9.6 |

FOREIGN PATENT DOCUMENTS

| | | | |
|---|---|---|---|
| EP | 932040 | * | 7/1999 |
| JP | 8015251 | | 1/1996 |
| WO | 84/02923 | * | 8/1984 |

* cited by examiner

Primary Examiner—Jill Warden
Assistant Examiner—LaToya Cross
(74) Attorney, Agent, or Firm—Mark M. Friedman

(57) ABSTRACT

A system to detect spoilage of a food product is described in this invention. The present invention can be used to see if a food product is spoiled, by mixing a part of the food product with an indicator of food spoilage within a separate transparent compartment of the food container, which is visible to the consumer.

10 Claims, 2 Drawing Sheets

FOOD FRESHNESS INDICATOR

FIELD AND BACKGROUND OF THE INVENTION

The present invention relates to indicators and, more particularly, to a system for visually indicating food spoilage in food containers.

There exist many known indicators of freshness of food products that indicate whether a certain food product may be spoiled. One of the prime indicators of food spoilage is microbial growth. On the other hand, some bacteria do not cause spoilage, but are actually added to milk or cream after pasteurization to make "cultured" products such as certain hard cheese. In those cases spoilage would be measured by looking for common pathogenic indicators such as salmonella or E. coli 0157.

There are indicators of microbial growth that change color only after the microbe grows. Chemicals that change color when pH changes have been used to mark the presence or absence of bacterial growth. Commonly utilized pH indicators include phenol red, bromocresol blue, and neutral red. Attempts have been made to measure bacterial growth using other than pH indicators. Markers, such as electrical impedance, electrical conductivity, amount of ATP (adenosine triphosphate), turbidity (optical density), have been measured from microbes growing in a general medium with the addition of a chemical that is measured. Tests for the above mentioned markers can be accurate but not practical for store and home detection of bacterial growth. Turbidity is practical for clear liquids and mostly only consumers with trained eyes except of course for extreme contamination where the supposedly clear liquid is completely cloudy.

A popular indicator for product freshness which is popularly extrapolated to indicate product spoilage when it shows predetermined signs is Time and Temperatures Indicators. In U.S. Pat. No. 5,182,212, Jalinski teaches one of numerous Time and Temperature Indicators which are operable to signal the attainment of one or more preselected time-temperature integrals which monitor the temperature and time history of a product utilizing a dual system of specific reaction pairs which simultaneously generate acid and alkali from two neutral substrates. One of the substrates is present in excess of the other. The preferred dynamic indicator system generates a constant pH buffer in the alkali range that is maintained until one of the substrates is depleted. At that time, a rapid pH change in the indicator solution to the acid range occurs, resulting in a very sharp visual color change in a pH-sensitive dye. The specific reaction pairs are enzyme/substrate pairs, preferably urease/urea and yeast/triacetin. A preferred combination pH-sensitive dye package includes m-nitrophenol, p-nitrophenol and litmus to provide an indicator which changes from green to reddish pink upon the expiration of a given amount of time at constant temperature, or in a shorter period of time, upon exposure to elevated abuse temperatures. In especially preferred embodiments, one of the enzyme substrate pairs includes an enzyme component provided by a microorganism which has been shock treated prior to incorporation in the indicator to improve temperature sensitivity and provide extended half life. The new and improved integratin indicators are adapted for use with packaged foodstuffs intended for refrigerated and room temperature handling and storage at temperatures between about 20° F. to about 120° F.

A TTI that is commercially available is sold under the trademark "LIFELINES" by Lifelines Inc. of Morris Plains, N.J. The US Army uses a "Bull's Eye" TTI label manufactured by Lifelines at a cost of $0.03 a label that help in the management of rations.

Amongst the disadvantages of TTI labels are that labels do exactly what they are named for. They give a picture of the time and temperature without any actual knowledge of what has transpired to the food product within the package, as the TTI labels are attached to the package's exterior. There is also room for fraud by exchanging food wrappers together with the TTI labels by any one involved in the whole chain from the food packers until the food arrives home to the consumer. Certain food products such as meat products, the TTI label is within the container in contact with the food product. The same disadvantages apply here as well wherein the label offers no information about any changes transpiring to the stored food product itself and fraud is still relatively easy.

When the food within a sealed container starts to spoil, several by-products are given off. It is therefore theoretically possible to detect spoilage by detecting one or more of these by-products. Common to all such deterioration is the production of heat, acidity, pressure, and carbon dioxide. Heat evolved during spoilage is small. Thus the typical conditions of storage and transportation of many food containers would produce temperature conditions far in excess of those likely to result solely from the heat released during spoilage. Pressure is perhaps a slightly more workable indicator, but still not very practical. In the first place, due to temperature variations and the chance of mishandling before sale, such a detector would have to be unresponsive to nominal pressure changes. Also, many products are heat sterilized after the can is sealed, so such a pressure detector would have to be insensitive to the pressure increase developed when the can is sterilized and would not be applicable to softer packaging. However, the development of substantial pressure occurs rather late in the spoilage process, and therefore, to be effective, it would be necessary for such a detector to respond to slight pressure increases. These are obviously conflicting requirements which make pressure detection impractical. Additionally, it would be very difficult to gauge any pressure changes in a packaging softer than a can.

As far as carbon dioxide is concerned, U.S. Pat. No. 4,003,709 to Eaton et al teaches providing a liquid impermeable pouch in which a liquid carbon dioxide detecting solution is entrapped. The solution provides a visually observable change when the concentration of carbon dioxide rises substantially above that which is the normal ambient concentration for our atmosphere. A suitable opening is formed in the container and the pouch is sealed into and over the opening so that the inert plastic material seals the opening and the microporous plastic portion is inside the container in at least gaseous contact or communication with the food contents. Thus, if carbon dioxide gas is generated it will pass through the microporous plastic and react with the calcium hydroxide to precipitate calcium carbonate. This causes the solution to change from clear to milky white, and this change is readily observable from outside the container by looking through the window. Visibility may be further enhanced by providing a coloring on the pouch opposite the window, such as green or blue. Such coloring provides a colored field which is visible until the carbon dioxide gas is produced. When the gas is produced, the observer sees the color of the window change from the color of the field to white, indicating that the food is probably spoiled and should not be consumed. The abovementioned pouch is not really mixed with the food contents and only reacts after the carbon dioxide gas permeates the microporous plastic portion which can be in a very miniscule and undetectable quantities in many cases of spoilage. As a related example, donated blood within blood bags which are suspect to be spoiled must be vigorously shaken in the bag for carbon dioxide to be detected in sufficient quantities in a similar carbon dioxide detection system. Shaking a food product vigorously of course would not be practical for food products.

U.S. Pat. No. 4,285,697 to Neary teaches a food spoilage indicator comprising a liquid crystal disposed in a carrier of plastic tape, at least one portion of which is semi-permeable to gases generated in food spoilage. His invention depends on the discovery that: (1) the appearance or color of a liquid crystal can be significantly altered by absorbed gas and/or (2) that liquid crystals can form micelles which can contain chemical indicators. It is almost always the case that when organic matter such as food is innoculated with bacteria or fungus or yeast and they start to multiply the process of decay is said to have started. Likewise it is always the case with bacterial or fungal or yeast initiated decay gas is evolved along with the toxins and other nitrogeneous compounds that cause food poisoning. The gases formed include: ammonia, hydrogen and carbon dioxide. Various organic acids may also be formed as well as nitrites which are usually intermediate. The rate at which these gases and/or other compounds are formed depends on the population of innoculant/contaminant because they are products of metabolism. Likewise the toxins and other compounds that cause illness are also metabolic products. Thus it is clear that if the gases and other benign compounds are formed in concert with those compounds that cause illness, then a measure of the former is indicative of the latter. If the food container holds an unacceptable level of bacteria, fungi or yeast, and the food presents an acceptable medium for growth, then the metabolic products mentioned above will be produced. Further if the porosity of the semi-permeable membrane is selected to pass only molecules whose size corresponds to the gas or gases or ions of interest and if the liquid crystal or admixture of liquid crystals or admixture of liquid crystals plus indicator (or reactant) is selected for its sensitivity to metabolic product of interest, then the liquid crystal or admixture of liquid crystals or admixture of liquid crystals plus indicator will change in appearance in proportion to the quantity produced of the metabolic product of interest passing through the semi-permeable membrane into the liquid crystal.

Acidity or pH was not a preferred index for Neary since the pH of various foods varies widely. It necessitated having a full spectrum of indicators in order to accommodate all the different pH levels of different kinds of foods.

According to "Venture", New York State Food Venture Center's Newsletter Summer 1998 Vol. 1 No.2 "More than 90 percent of the scheduled processes approved by the Food Venture Center (FVC) require the processor to check the pH of the product before it is bottled or shipped. Since the pH is often the determining factor whether or not the product will be safe to consume, it is very important that testing be done correctly and accurately . . . . By law, if product pH is less than 4.0, it can be checked with simple pH papers (often called litmus strips). This method is inexpensive, but it has drawbacks. Firstly, if the product tested is thick or highly colored, the color of the strip may not be easy to determine. Secondly, if the product pH is normally close to 4.0 say 3.8 or 3.9 you may not be able to detect a formula deviation that sends the product above its safe pH level. Thus, it is our position that a wise manufacturer invests in a good pH meter!" It is obvious from this that a pH measurement of the food product performed as close as possible to the time of consumption would be greatly advantageous in the prevention of the dangers of eating spoiled foods.

As it is not practical to perform pH or other indicator measurements at the consumer's house, in addition to the fact that the average consumer does not know (or want to know) the pH of the food product to be consumed, it would be highly advantageous to be able to ascertain a significant change in pH or other indicator level of the product in the store before purchasing the product or consumption of the food product after purchase. A solution to the practicality problem would be to have a small portion of the food in a separate cell within or attached to the food container visible from the outside mixed with an indicator which would change color if the food in the container was showing signs of spoilage which would be detected by the particular indicator chosen for the product. Any change in the pH or any other indicator of spoilage would be visible from the exterior of the container and would in essence be a warning to the consumer not to purchase or consume the product whereas no color change in the appearance of the food as seen from the outside would indicate to the consumer that food product is suitable for purchase and consumption.

SUMMARY OF THE INVENTION

According to the present invention there is provided A system for indicating a status of a quality of a food product. The system including an indicator which is mixed with at least a portion of the food product.

According to further features in preferred embodiments of the invention described below, the status of the quality of the food product is selected from the group consisting of recommended for consumption, questionable recommendation for consumption and not recommended for consumption.

According to still further features in the described preferred embodiments, the food product is selected from the group consisting of processed food, soft drinks, fruit drinks, alcoholic drinks, wine, drink concentrates, dairy products, fresh agricultural produce, fish products and meat products.

According to still further features in the described preferred embodiments, the indicator is an indicator capable of indicating a change in pH.

According to still further features in the described preferred embodiments, the indicator is capable of detecting a product of spoilage of the food product.

According to still further features in the described preferred embodiments, the indicator irreversibly changes at least one of its properties upon change in the status of the quality of the food product.

According to still further features in the described preferred embodiments, the wherein the food product is contained in a container.

According to still further features in the described preferred embodiments, the container has at least two compartments.

According to still further features in the described preferred embodiments, the indicator includes an encapsulated indicator.

According to still further features in the described preferred embodiments, the at least two of the at least two compartments are joined by a valve permitting movement of food in one direction only.

According to still further features in the described preferred embodiments, the indicator is mixed with the at least a portion of the food product in at least one of the at least two compartments.

The present invention successfully addresses the shortcomings of the presently known configurations by providing a separate transparent compartment of a food container, which is visible to the consumer and mixing a part of the food product with an indicator of food spoilage.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
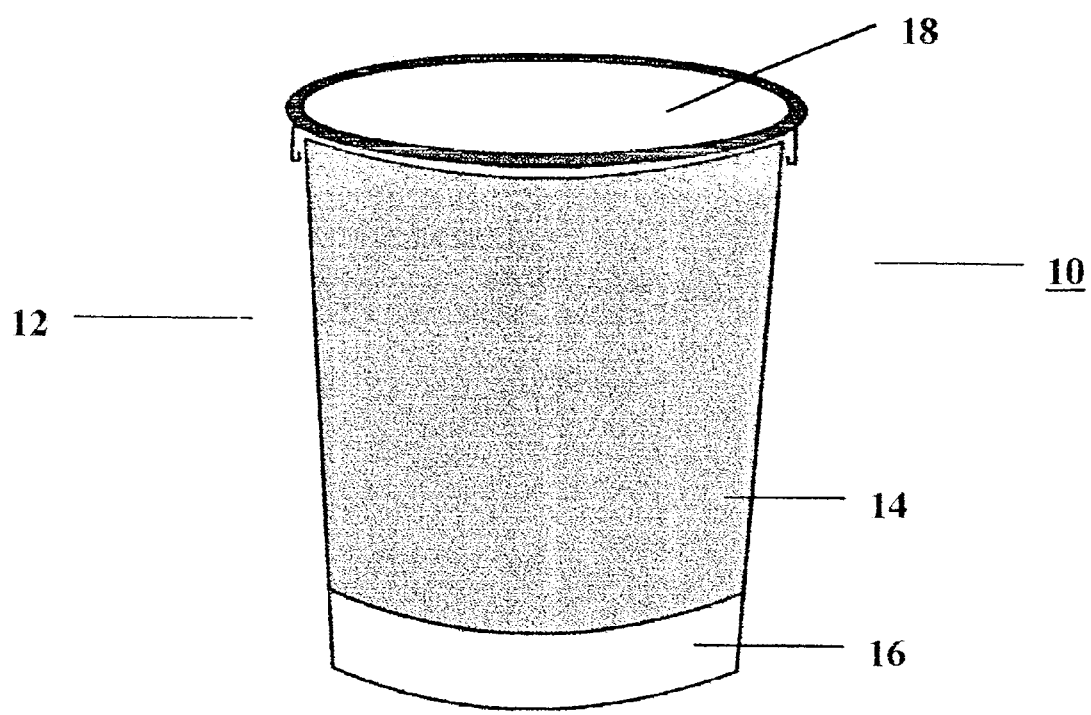
FIG. 1 is a schematic representation of a container of a food product, with a separate transparent compartment containing at least a portion of the food product mixed with an indicator.

The present invention is of a system, which can be used to detect spoilage of a food product. Specifically, the present invention can be used to see if a food product is spoiled by mixing a part of the food product with an indicator of food spoilage within a separate transparent compartment of the food container visible to the consumer.

The principles and operation of a system for visually indicating food spoilage in food containers according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Before explaining at least one embodiment of the invention in detail, it is to be understood that the term "food product" includes, but is not limited to processed food, soft drinks, fruit drinks, alcoholic drinks, wine, drink concentrates, dairy products, fresh agricultural produce, fish products and meat products.

Figure 2:
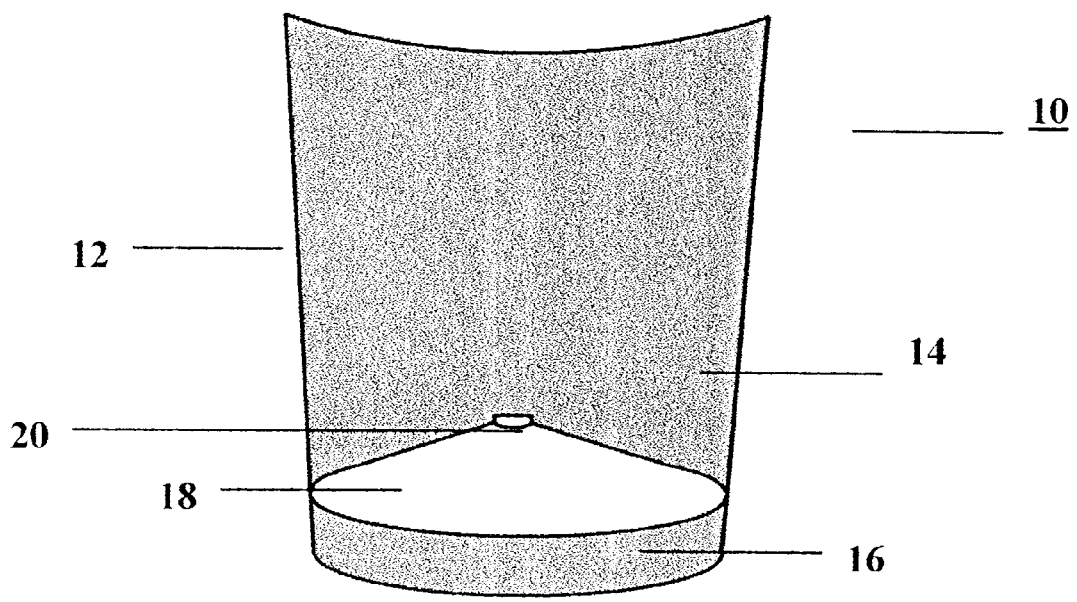
FIG. 2 is a cross section of a container of a food product, with a separate transparent compartment containing at least a portion of a food product mixed with an indicator, showing a compartment separator with a single-directional valve.

Referring now to the drawings, FIG. 1 illustrates a system 10 for indicating a status of a quality of a food product. System 10 includes an indicator mixed with at least a portion of the food product. The food product is shown in container 12. Container 12 illustrated here has two compartments, main compartment 14 containing food to be consumed by the customer and smaller compartment 16 containing a small portion of the food product mixed with an indicator. Small compartment 16 is separated from main compartment 14 by partition 18 (FIG. 2). Food introduced into container 12 passes through single-directional valve 20. An indicator of food spoilage such as a pH indicator is already present in smaller compartment 16 so that when the food product passes through the single-directional valve it mixes with the indicator. In another preferred embodiment, the indicator is encapsulated into capsules. Smaller compartment 16 has a transparent wall, such that any change in the color of an indicator can be easily discerned from just observing container 12.

A typical indicator for a milk product could be a mixture of three parts of phenol red and one part methylene blue known to Food Technology students as Ulrich Milk. Phenol red is red at alkaline pH. Phenol red is yellow at acid pH. Oxidized methylene blue is blue. Reduced methylene blue is colorless. Recall red plus blue is purple. Unspoiled milk in this embodiment will show a medium bluish-gray color in smaller compartment 16 mixed with abovementioned mixture of phenol red and methylene blue. Slightly acidic milk will give a pale yellow-green, acidic with reduction will give a pale-yellow orange. On the other end of the pH scale, and spoiled milk in the alkaline range will give a purple color, and alkaline with reduction gives a red color. There are more than 67 pH indicator fluids on the market. A company that sells an immense variety of these fluids as well as test papers is Micro Essential Laboratory, in Brooklyn, telephone 718/338-3618, fax 718/692-4491. As pH values for various food products greatly vary, it will be appropriate to formulate a concoction of pH indicators that will suit each and every food within its container. It is possible for one skilled in the field of food technology to find an indicator for each particular food product.

In a preferred embodiment, the color of the normal pH for the particular food product will be colorless and only when a higher or lower pH is obtained in the food product which will serve as an indication of spoilage, will the food in smaller compartment 16 irreversibly change from a colorless color to a red color. This red color appearing in smaller compartment 16 would indicate to the consumer that the food product was unsuitable for purchase and consumption. Other indicators could detect presence of certain toxins or particular pathogenic bacteria such as *E. coli* 0157, Salmonella, enterotoxigenic staphylococci, and Listeria.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A system for retail packaging of a food product indicating to a consumer a status of a quality of the food product, the system comprising:
    (a) a container having a first compartment containing a first portion of the food product for consumption by the consumer and a second compartment containing a second portion of the food product; and
    (b) an indicator, said indicator mixed with the portion of the food product in said second compartment.

2. The system of claim 1, wherein the status of the quality of the food product is selected from the group consisting of recommended for consumption, questionable recommendation for consumption and not recommended for consumption.

3. The system of claim 1, wherein the food product is selected from the group consisting of processed food, soft drinks, fruit drinks, alcoholic drinks, wine, drink concentrates, dairy products, fresh agricultural produce, fish products and meat products.

4. The system of claim 1, wherein said indicator is an indicator capable of indicating a change in pH.

5. The system of claim 1, wherein said indicator is capable of detecting a product of spoilage of the food product.

6. The system of claim 1, wherein said indicator irreversibly changes at least one of its properties upon change in the status of the quality of the food product.

7. The system of claim 1, wherein said first and second compartments are joined by a valve permitting movement of the food product in one direction only from said first compartment to said second compartment.

8. The system of claim 1, wherein said indicator includes an encapsulated indicator.

9. The system of claim 1, wherein at least part of a wall of said second compartment is transparent.

10. The system of claim 1, wherein said first compartment is larger than said second compartment.

* * * * *